United States Patent
Pinhack et al.

(10) Patent No.: US 6,627,451 B2
(45) Date of Patent: Sep. 30, 2003

(54) PROCESS AND DEVICE FOR MEASURING COMBUSTION HEAT IN A CALORIMETRIC BOMB

(75) Inventors: Hubert Pinhack, Bad Krozingen (DE); Armin Wiesler, Staufen (DE); Alf-Bernd Ambs, Gutach (DE)

(73) Assignee: IKA-Werke GmbH & Co., KG, Staufen (DE)

( * ) Notice: Subject to any disclaimer, the term of this patent is extended or adjusted under 35 U.S.C. 154(b) by 281 days.

(21) Appl. No.: 09/861,028

(22) Filed: May 18, 2001

(65) Prior Publication Data

US 2002/0013001 A1 Jan. 31, 2002

(30) Foreign Application Priority Data

May 18, 2000 (DE) .......................................... 100 24 147

(51) Int. Cl.[7] .............................................. G01N 25/20
(52) U.S. Cl. ...................... 436/147; 436/180; 436/157; 422/51; 374/31; 374/33; 374/39; 374/40
(58) Field of Search ................................. 436/147, 180, 436/157; 422/51; 374/31, 33, 39, 40

(56) References Cited

U.S. PATENT DOCUMENTS

| | | | |
|---|---|---|---|
| 4,925,315 A | * | 5/1990 | Bonnard ...................... 374/31 |
| 5,322,360 A | * | 6/1994 | Willis et al. ................... 374/38 |
| 5,547,282 A | * | 8/1996 | Pinhack et al. ............... 374/36 |

FOREIGN PATENT DOCUMENTS

DE            3220842 A1    12/1983

* cited by examiner

*Primary Examiner*—Jan Ludlow
*Assistant Examiner*—Sam P. Siefke
(74) *Attorney, Agent, or Firm*—Volpe and Koenig, P.C.

(57) ABSTRACT

A water bath accommodating a calorimetric bomb (2) for measuring the combustion heat of substances with the aid of a calorimeter. The inner tank (3) is enclosed by an outer container (5) forming a water jacket and is shielded from the environment. If several measurements are conducted subsequently, the water found in the inner tank (3) and heated above its initial value through the combustion process taking place in connection with a previous measurement can be at least partially transferred into the outer container (5) with a second or other succeeding measurement prior to conducting it so that at least a part of the combustion heat of the preceding measurement can be used for heating up at least the water jacket in the outer container (5) in connection with the next measurement. Consequently, energy for tempering the water in the water jacket and/or in the water bath can be saved.

15 Claims, 2 Drawing Sheets

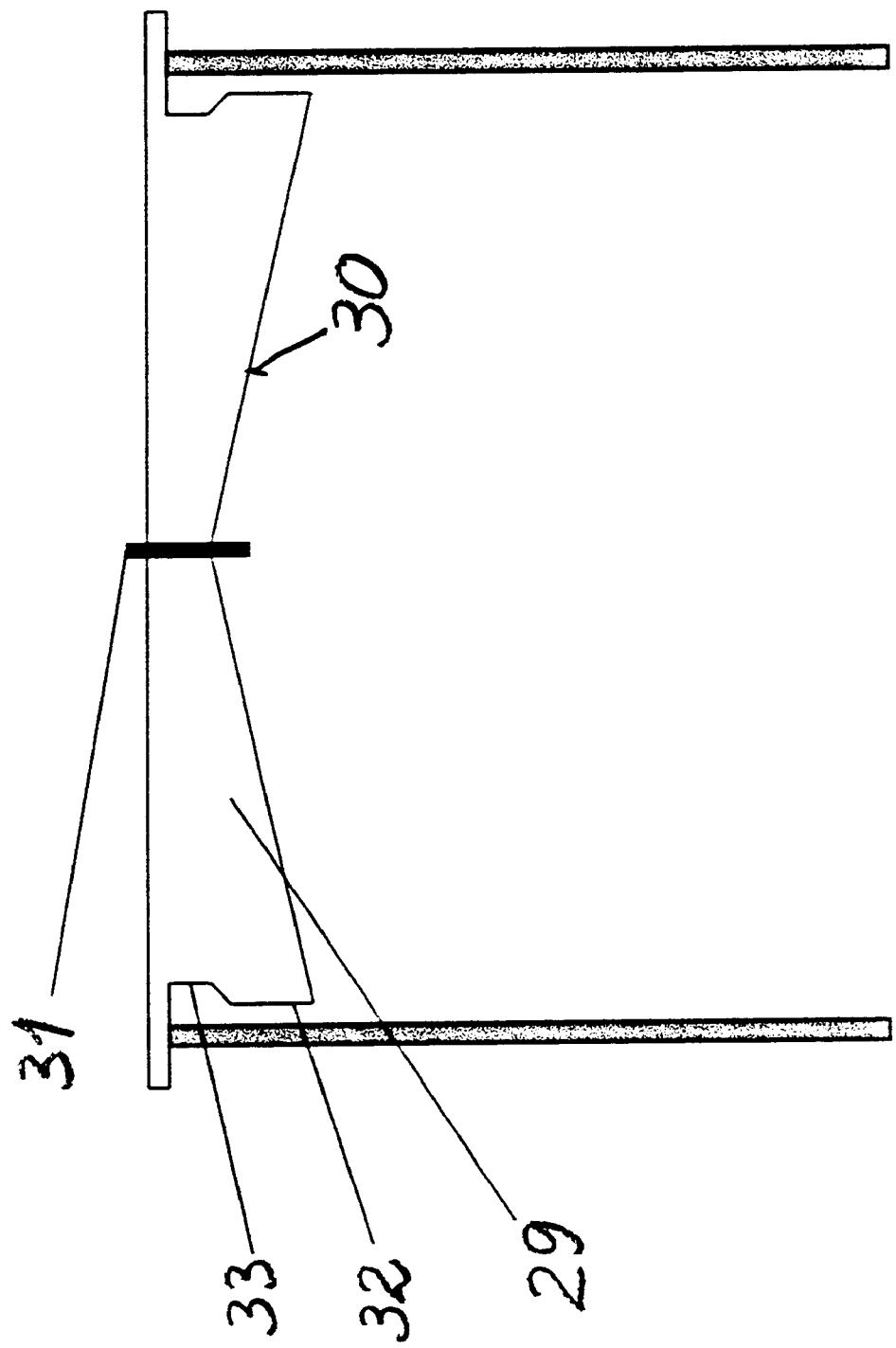

PROCESS AND DEVICE FOR MEASURING COMBUSTION HEAT IN A CALORIMETRIC BOMB

BACKGROUND

Figure 1:
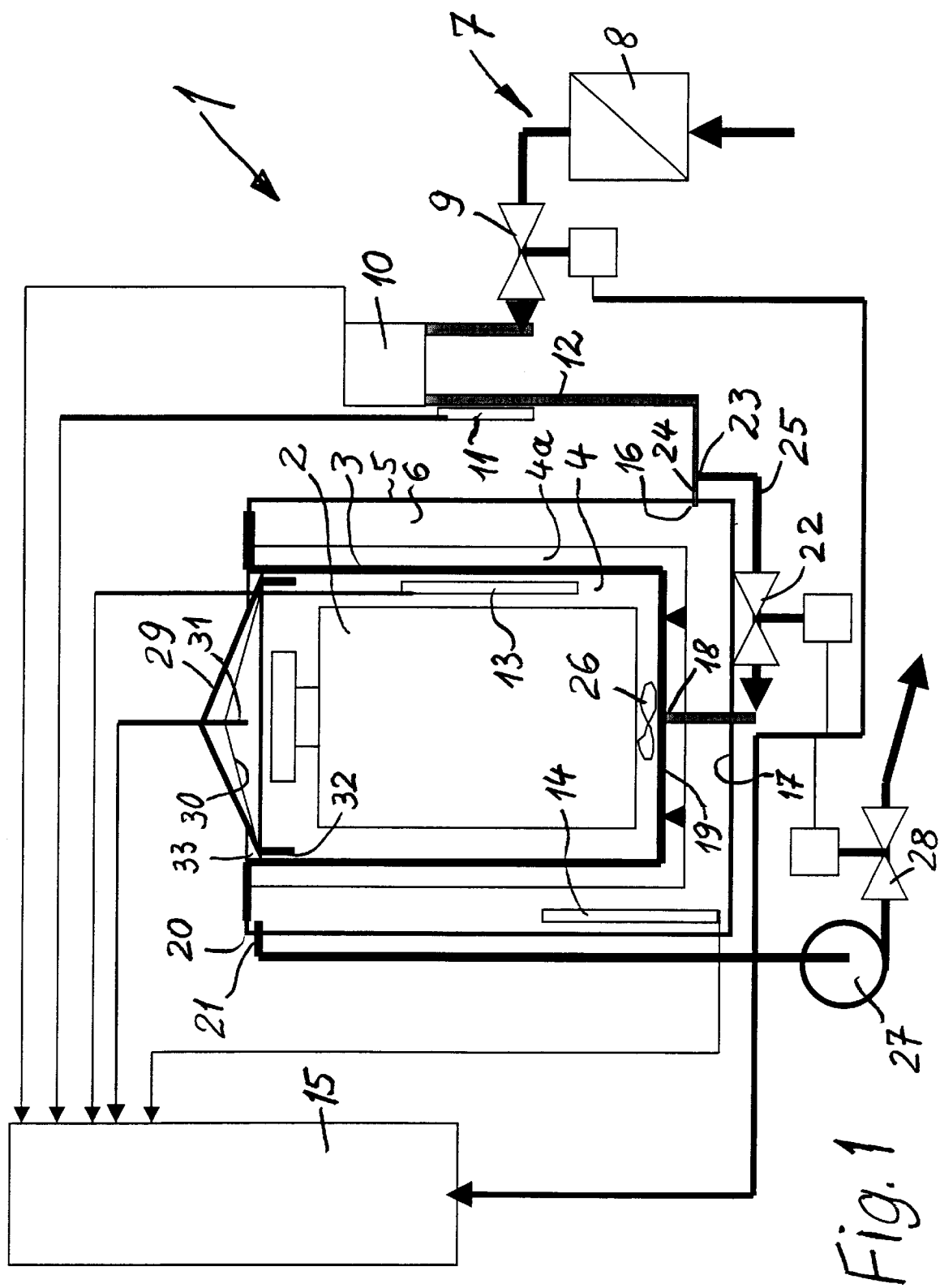

The invention concerns a process for measuring combustion heat of substances which are fed into a calorimetric bomb and burned in this, whereby the calorimetric bomb is placed, prior to igniting the combustion process, in a water bath situated in an inner tank and this water bath for its part is enclosed by a water jacket situated in an outer container, and whereby a distance is provided between the two bodies of water in the water bath and in the water jacket, and a temperature differential is set, and whereby after, for example, a first measurement, at least one further measurement of the combustion heat of the same and/or of another substance is conducted.

The invention furthermore concerns a device for conducting this process, namely a calorimeter with an internal tank accommodating a calorimetric bomb and with an outer container enclosing this at a distance for accommodating the water jacket as well as with a water feeder to the inner tank and the outer container, and with a water drain at least on the outer container, and furthermore with a heating device arranged in the water feeder which is preferably joined with a controller or a regulating device whereby temperature sensors are arranged in the outer container and the inner tank which are connected with the regulating device for the water feeder.

A process of this type and a device of this type are known from practice. Here, as a rule cold or cool water is at first fed into the outer container through a regulated continuous flow heater whereby the temperature sensor present there ensures that the desired temperature is attained in the water jacket formed by filling the outer container. Here, if the occasion arises, it can be necessary to continue the filling process until the water introduced overflows through a drain, especially in the upper region of this outer container, and the water remaining in this outer container reaches the temperature sought. Then a valve or similar closing means can be shut off by the controller.

After this, filling of the inner tank takes place with the same temperature adjusted on the continuous flow heater.

This method and corresponding calorimeter have proven themselves because the regulating expenditures as well as the expenditures in equipment are relatively low. Nevertheless, however, very exact combustion values can be determined.

Of course, with any measurement, a considerable energy consumption for the continuous flow heater is necessary again and again in order to set the exact temperature for each measurement which also can change again and again with successive measurements since the calorimeter can always contribute a certain warmth itself on the basis of previous measurements.

A process and a device for filling the inner tank of a combustion calorimeter are known from DE 32 20 842 A1, whereby a water storage container with a heating device and a temperature regulation unit for it are provided in order to temper the water for filling the inner tank beforehand. Even here a considerable energy consumption is necessary for heating this storage container.

For this reason, there exists the object of creating a process and a device of the above-mentioned type where energy for the continuous flow heater and if need be also time for setting the exact temperature differential can be saved.

SUMMARY

For accomplishing this object, one proceeds such that before the measurement following a previously conducted measurement, the water situated in the inner tank heated above its initial value through the preceding combustion process is at least partially transferred to the outer container, and consequently at least a portion of the combustion heat is used for heating up at least the water jacket in the outer container, and in that then the inner tank is refilled or filled up and the temperature differential is adjusted.

Thus, the combustion heat is used in an advantageous and appropriate manner to temper at least the water jacket so that when filling the water jacket for such a successor measurement, the continuous flow heater is not needed or hardly needed. That means, with such a successor measurement, the energy of the continuous flow heater can be wholly or at least be partially saved for filling the water jacket. If in this connection an excessively high temperature arises in the water jacket, then merely unheated, thus cold water, needs to be added to reach the temperature sought.

For the simplest possible procedure which also requires appropriate time, it is beneficial if preheated water from a continuous flow heater or normally temperature-stabilized water is fed into the inner tank upon filling up for the next measurement following upon a measurement, and if cold and/or not heated water is fed to the outer jacket filled with heated water for adjusting the temperature of the water jacket, and the excess amount of water resulting from this is drained off until the water jacket has reached the sought temperature. The method for adjusting the temperature differential is thus similar to the inherently already known method whereby; however, due to the utilization heat of a preceding measurement, energy is saved. The energy saving can in this manner still be improved in that the inner tank also contains at least a residue of water which was additionally heated by the previous combustion process, whereby a portion of this water is transferred to the outer container, but a remainder can remain in the inner tank and for its part be supplemented and mixed with cold water in order to produce the proper temperature differential.

It is thus especially energy saving if only a portion of the water heated in connection with a measurement is loaded out of the inner tank into the outer container, and a remainder of the water heated by the measurement is left in the inner container, and if the inner tank and the outer container are replenished with cold water, and the water in the inner tank and in the outer container are mixed such that the temperature differential required for a further measurement is formed. In this way, the water to be replenished can be completely untempered so that an energy-consuming preheating of the water required to replenish the outer container and the inner tank can be completely dispensed with.

In this connection, it can be advantageous if so much water heated by a combustion process is moved out of the inner tank into the outer container that the water situated in the outer container has an excessively high temperature for the next measurement, and that the exact temperature differential in relation to the inner tank is adjusted by replenishing by cold or not tempered water. Due to the previous combustion process, the inner tank contains heated water such that with this in the outer jacket, an at first excessively high temperature can be adjusted so that setting the exact temperature to a certain extent can be downwardly adjusted from an excessively high initial value which can be accomplished in a very simple manner by mixing in cold water-if need be in connection with simultaneous mixing or stirring of this water, whereby advantageously with this type of temperature adjustment, no more outside energy is needed.

The temperature in the inner tank and in the outer container can be measured when transferring heated water into the outer container and when replenishing with cold water, and introducing the water to be replenished can be regulated through valves or the like. In this way, the introduction of the amount of cold water can be adapted to the requirements in question without having to allow for a great loss of time.

An especially advantageous refinement of the process of the invention can include that during filling and setting the temperature in the inner tank, the temperature of the water is recorded and determined by a computer in anticipation, and in that the tempering of the water in the outer container takes place before the end of the temperature balancing in the inner tank between the added water, the calorimetric bomb and the inner partition.

Through this method and the advance calculation of the mix temperature, time can be saved in connection with the preparation and implementation of the measuring process. At the same time, the temperature of the calorimetric bomb and the entire calorimeter can be taken into consideration in this connection which accordingly has an effect upon the mixture temperature of the water.

The device mentioned at the beginning serving to conduct the process for accomplishing the object can be characterized in that the water feed to the outer container and to the inner tank is at all times arranged in the lower region, and in that a drainage or overflow is arranged in the region of the upper edge of the outer container, and the feed to the inner tank is alternatively usable as a drain. Consequently, a single water feed results which is usable through the appropriate valves for feeding the outer container and the inner tank, and is also usable for transferring water out of the inner tank into the outer container.

At the same time, it is beneficial if a single water feed is provided with a branching, and in any given case, a feeder leads from the branching to the outer container and an additional feeder leads to the inner tank, and the branch for supplying the inner tank usable as a drain is closably connected through a valve with the branching and the feeder branch to the outer container. This results in a conduit guide which can be manufactured relatively simply and in a space-saving manner and is also relatively operable through control devices in order to fill the outer container and the inner tank in the sequence necessary to implement the process, or to transfer water out of the one container into the other and then once again to be able to be able to mix with fresh water.

Here, a continuous flow heater is arranged in the feed in front of the branch for tempering the water introduced for the necessary tempering of the water in connection with an initial tempering, so that the inner tank as well as the outer jacket can be filled with appropriately heated water if combustion heat is not yet available from a preceding measuring process or, however, in the course of a measuring series, a retempering of the feed water nevertheless becomes necessary owing to a somewhat long interruption.

The water feed for the water can advantageously and simply be connected or connectable with a typical stationarily installed water conduit. Consequently, the device can be installed everywhere in a simple manner wherever it is needed or is appropriate insofar as a water conduit is available or will possibly correspondingly be laid.

For an exact measurement, it is appropriate if the partition at least of the outer container is heat insulated.

An appropriate configuration of the device can be provided in that in the inner tank, especially for regulating or adjusting the water temperature, an agitator is arranged for rotating the water situated in the inner tank and, preferably in an outlet conduit, a pump is arranged. While the agitator ensures a rapid intermixing of the water in the inner tank and intermixture, takes place in the outer container through the inflow technique, the pump in the outlet conduit of the outer container can accelerate the process of pumping the excess water out of the outer container if this must be overfilled when setting an exact temperature and temperature differential.

In the outflow conduit of the water which can be sucked or discharged out of the outer container, a valve which is closed during measurement can be arranged behind the pump. If in contrast water should be let out, this valve can also be opened.

For the exactitude of filling with the necessary amount of water, especially of the inner tank, it is appropriate if a cover is arranged on the upper side of the inner tank which, on its underside facing the interior of the inner tank, bounds a space conically tapering especially upwardly, on the highest point of which a filling level sensor is arranged, and if this cover is sealed off in relation to the inner tank through a capillary slot. In this way, a precise filling can thus take place in the interior of the inner tank where already the slightest level deviations of the tapering space of the cover can be recognized by the filling level sensor, and if need be can correspondingly be compensated for. The capillary slot brings about a good sealing, nonetheless makes possible, however, an overflow of the water in the event that this is expanded owing to heating. It can thus be ensured that the inner tank is sealed off by the cover such that no fluid can exit, but that the position of the cover and the inner volume always agree for repeatable fillings.

At the same time, an additional annular slot or similar space can be arranged above the capillary slot for accommodation of the water exiting owing to expansion during heating. Consequently, the overall amount of water itself then remains preserved if the water of the inner tank expands due to heating. With the aid of the filling level sensor situated on this cover, the water feeder or a filling level valve situated in this can be closed off in any case if the free residual volume not filled up by water in the tapering space of the cover is negligibly small. Slight fluctuations in height of the water level at this place consequently have practically no noticeable effect on the overall volume, and consequently also not on the measurement.

Chiefly in the combination of single or several of the previously described features and measures, there thus results a calorimeter with a vessel for sampling and combusting the sample under increased oxygen pressure, an inner tank for accommodating this vessel and for accommodating a certain amount of water as well as a temperature sensor for measuring the temperature in this inner vessel with an external outer container which is filled with tempered water and in which the inner tank is mounted through an air gap or distance as insulation and through fixation by bracings, and is surrounded by this, and serves for energetic decoupling from the environment. Here, the water from the water conduit or if need be also out of another external water feeder can be heated for tempering by a heat exchanger by opening the shutoff valve as long as such water flows toward the discharge through the outer tank though the pump and/or a valve until the necessary temperature is reached. After this temperature is reached, the inner tank is filled up by opening a valve inside the water feeder and by closing the valve at the outlet of the outer container, and after reaching the filling level sensor arranged in particular within the tapering space of a cover, this valve is closed again, whereby readiness for measuring is attained. With a subsequent measurement and additional consequent measurements, the heated water situated within the device and in particular also the combustion heat arising, which further heats up at least the water in the inner tank, can be used in order to set the proper initial temperature and initial differentials without, nonetheless, the necessity of heating up added water.

Advantageously, the warm up times are dispensed with which would otherwise accrue if the calorimeter is shut off during a pause. During the measurement in and the pauses, no water needs to be tempered or rotated which means a lower energy consumption, at least during measurement.

BRIEF DESCRIPTION OF THE DRAWING(S)

An embodiment of the invention is described in greater detail below on the basis of the drawings. Shown in schematic representation are:

FIG. 1 is an elevational view of a device with a calorimeter, an inner vessel, the inner tank accommodating this and outer container as well as corresponding feed conduits, sensors valves and FIG. 2 is an enlarged scale view of the upper edge of the inner tank with the cover sealing this off, the space conically tapering upward on its underside and which has, at the highest point of this space, a filling level sensor.

DETAILED DESCRIPTION OF THE PREFERRED EMBODIMENT

A device schematically represented in FIG. 1, designated overall with 1, namely a calorimeter, hereinafter designated as "device 1" or as "calorimeter 1," serves to measure the combustion heat of substances which can be loaded into a calorimetric bomb 2 forming a vessel serving to accommodate samples which can also be designated as a treatment vessel, and combusted therein. The calorimetric bomb 2 is here placed in a water bath 4 situated in the inner tank 3 prior to ignition of the combustion process. That means that an inner tank 3 accommodating the calorimetric bomb 2 also belongs to device 1 or to calorimeter 1.

Furthermore, an outer container 5 for accommodating a water jacket 6 which encloses the inner tank with an intermediate space or distance 4a also belongs to calorimeter 1, owing to which the inner tank 3 and its water bath 4 are thermally shielded and closed off from the environment.

A water feed designated as a whole with 7 to the inner tank 3 and to the outer container 5 contains a continuous flow regulator 8, a shutoff valve 9 regulated in the embodiment and a continuous flow heater 10 for stabilizing the temperature of the water from the water feed 7 which can also come from a water reservoir or the water conduit before this water is poured into the inner tank 3 and the outer container 5 for an initial measurement.

At the same time, in the embodiment, a temperature sensor 11 is arranged in the conduit directly connecting to the continuous flow heater 10, a temperature sensor 13 is arranged in the inner tank 3, and a temperature sensor 14 is arranged in the outer container 5.

The continuous flow heater 10 arranged in the water feed 7 as a heating device is moreover connected with the control unit or with a regulating device, just as the temperature sensors 11, 13 and 14 mentioned, so that specified standard values of temperatures are compared with actual values and can be correspondingly adjusted.

The water feed 7 to the outer container 5 and to the inner tank 3 is here at all times arranged in their lower region, and one will recognize in FIG. 1 the aperture 16 of the water feed 7 into the outer container 4 near its lower floor 17 while the aperture 18 of the water feed 7 into the inner tank 3 is arranged on its floor 19.

In contrast, a drain or overflow 21 is arranged in the region of the upper edge 20 of the outer container 5. Consequently, the outer container 5 can be filled and overfilled by introducing water through the water feed 7 and the aperture 16. Thus, excess feed water can be discharged again through the overflow 21 in order, for example, to adjust in the outer container 5 a mixture temperature of the water bath 6 present there.

In a yet to be described manner, the feeder to the aperture 18 and therewith to the inner tank 3 is moreover switchable and is also usable as a discharge so that, through the aperture 18, the inner tank 3 can also be emptied and the water contained in it can be directed in a manner still to be described through a valve 22 to the aperture 16 into the outer container 5.

The water feed 7 has in the course of the conduit 12 a branching 23 from which in each case a feeder 24 to the aperture 16 and consequently to the outer container 5, and a further feeder 25 over the valve 22 is to be opened for emptying the inner container 3 so that the content of the inner tank 3 can at first pass through the valve 22 and the feeder 25 as well as the branching 23 into the outer container 5, from which it can correspondingly flow out or displace the contents of the outer container 5 through the overflow 20 and the conduit 21.

As mentioned already, the continuous flow heater 10 is moreover arranged in the feeder conduit 12 in front of the branching 23 for tempering the water introduced. At the same time, the water feed 7 can be connected with a typically stationarily mounted water conduit or a water tank or similar reservoir and be adjusted with respect to the amount continuously flowing with the aid of a continuous flow regulator 8.

In order to shield the inner tank 3 as best as possible from the environment, the partitions at least of the outer container 5 are also heat-insulated. In the inner tank 3, an agitator 26 for rotating the water situated in the inner tank 3 is provided for controlling or adjusting the water temperature, so that when mixing of, for example, warmer water previously found in the inner tank with cold water, a balanced mixing temperature can rapidly be reached. In the outlet conduit 21 of the outer container 5, a pump 27 is arranged in the preferred embodiment which can conduct or support the pumping out of excess water out of the outer container or the system of the outer container 5 and inner container. It is also conceivable, however, to bring about the discharge of water out of the outer container 5 by gravity. At the same time, a valve 28 which is closed during measurement is arranged behind the pump 27 in the outflow direction of the water which can be sucked or discharged from the outer container 3, which is opened when the water is discharged. In order that the processes can run largely automated, valves 9, 22, and 28 are constructed here as control valves which are connected with the controller 15.

In FIGS. 1 and 2, one will recognize on the upper side of the inner tank 3 in any given case an outwardly somewhat variously configured cover 29 which delimits on its underside facing the interior of the inner tank 3 a space conically tapering upwardly. This interior of the cover 29, constructed as a negative cone, is designated as 30 in FIG. 2. A filling level sensor 31 is arranged at the highest point of this interior 30 conically tapering upward which ensures that when filling the inner tank 3, a level practically equal for each measurement is obtained due to the conical interior 30. Even the slightest differences in level have the corresponding effects due to the conical interior 30 so that the volume found in the inner tank 30 can always be set in a repeatable manner.

In order moreover to consider the expansion of water due to heating, the inner tank 3 is sealed off through a capillary slot 32 which is formed between the exterior of the cover and the upper interior in the edge region of the inner tank 3, and is represented overly broad in FIG. 2. A tightness is thus produced at this site. Nevertheless, however, an expansion of the content of the inner tank is made possible.

Above the capillary slot 32, one will recognize an additional annular slot 33 of enlarged cross section which serves as a space for accommodating water exiting upward due to expansion out of the annular slot 32 during heating. If the heating diminishes again, this water can also run back again. Moreover, this compensation space is situated higher than the highest place of the conically tapering space on the underside or interior 30 of the cover 29.

It is possible to operate advantageously with the device 1 such that after an initial measurement of a combustion heat within the calorimetric bomb 2, the water situated in the inner tank 3 and warmed above its initial value through the combustion process is at least partially transferred to the outer container 3 since the valve 22 is opened and the pump 27 is put into operation. Consequently, at least a part of the combustion heat generated with a preceding measurement is used to heat at least the water jacket in the outer container 5 which at first has an increased temperature owing to this transfer. The inner tank 3 can then be filled again or filled up, and the temperature differential in relation to the outer container 5 can be adjusted.

Moreover, preheated water from the continuous flow heater 10 or normally tempered or cold water can be introduced to the inner tank 3 upon renewed filling for a subsequent measurement following upon a measurement according to how much of the water additionally heated by the combustion was transferred from the inner tank 3 into the outer container 5. Cold and not heated water can be introduced to the outer container 5 filled with heated water for adjusting the temperature of the water jacket through the branching 23 and the aperture 16 with a closed valve until the proper mixture temperature is set, whereby the excess water arising in this way is discharged through the overflow 20. Cold water can thus be introduced into the outer container 5 which contains excessively warm water from the inner tank 3 until enough is displaced by the warm water to obtain a mixture temperature which stands in the proper difference to the temperature of the water in the inner tank 3.

Here it is also possible to transfer only a portion of the heated water in connection with a measurement from the inner tank 3 into the outer container and to leave a remainder of the water additionally heated owing to the measurement and then replenish the inner tank 3 and the outer container 5 at all times in appropriate sequence with cold water and thus mix its content with cold water. Here the water in the inner tank 3 and the water in the outer container 5 can be mixed in any given case such that the temperature differential necessary for a further measurement is formed and set. This can moreover in any given case be checked with the aid of the temperature sensors 13 and 14, measured and also appropriately regulated through the control unit 15.

Appropriately, as much water heated by a combustion process can here be transferred out of the inner tank 3 into the outer container 5 such that excessively warm water, thus water with a temperature too high for the next measurement, is contained in the outer container 5. The exact temperature differential in relation to the inner tank 3 or its content can then be adjusted by replenishment of cold or non-tempered water while the valve 22 is closed over the aperture 16 so that the exact temperature setting can take place in an advantageous manner in the outer container 5 through a cooling process where the introduction of electric energy, for example, through the continuous flow heater 10 is not necessary so that in successor measurements following an initial measurement, the combustion heat at all times suffices for renewed setting of the correct temperature, and the continuous flow heater 10 and energy fed to this are not needed.

The temperature in the inner tank 3 and in the outer container 5 can moreover be measured when transferring heated water into the outer container 5 and when replenishing with cold water, as already mentioned, with the aid of temperature sensors 13 and 14, and the introduction of the water to be replenished can be regulated through valves 9, 22 and 28.

With the previously described process, the temperature of the calorimetric bomb 2 and the entire calorimeter 1, thus also, for example, the inner tank and the outer container 5, can also be taken into consideration, and time can be saved since already during filling the inner tank 3 with water, its temperature is recorded and determined by a computer in anticipation of the resulting mixture temperature, as the actual water temperature and the amounts of heat of the parts coming into contact with this water are subject to an appropriate lawfulness. The tempering of the water in the outer container 5 can in this way already take place prior to the end of the actual temperature balance in the inner tank 3 between the water introduced, the calorimetric bomb 2 and the inner partition.

A water bath in an inner tank 3 accommodating the calorimetric bomb 2 serves for measuring the combustion heat of substances with the aid of a calorimeter, whereby the inner tank 3 is enclosed by an outer container 5 forming a water jacket and shielded from the environment. If several measurements are successively conducted, with a second or other following measurement, the water found in the inner tank 3 and heated above its initial value through the combustion process which took place in connection with a preceding measurement is transferred at least partially into the outer container 5 prior to conducting it so that at least a portion of the combustion heat of the preceding measurement can be used for heating up at least the portion of water in the outer container 5 in connection with the next measurement. Consequently, the energy for tempering the water in the water jacket and/or in the water bath can be saved.

What is claimed is:

1. Process for measuring the combustion heat of substances which are loaded into a calorimetric bomb (2) and combusted comprising, prior to igniting a combustion process placing the calorimetric bomb (2) in a water bath (4) situated in an inner tank (3), enclosing the water bath with a water jacket situated in an outer container (5), providing a distance between both bodies of water in the water bath and in the water jacket and setting a temperature differential, and conducting an initial measurement, then at least partially transferring the water situated in the inner tank (3) that is warmed above an initial value by the initial combustion heat measurement into the outer container (5), and using at least a portion of the combustion heat for heating up at least the water jacket, then refilling the inner tank (3) and adjusting the temperature differential, and conducting at least one further measurement of a combustion heat.

2. Process according to claim 1, further comprising feeding the inner tank (3) preheated water out of a continuous flow heater (10) or normally temperature-stabilized water when filling up for a subsequent measurement following upon the initial measurement, and feeding the outer container (5) filled with heated water cold and/or not heated water for setting the temperature of the water jacket, and discharging the excess water resulting from this until the water jacket has reacted the initial temperature.

3. Process according to claim 1, wherein only a part of the water heated in connection with a measurement is transferred from the inner tank (3) into the outer container (5) and a remainder of the water heated by the measurement is left in the inner tank (3), and further comprising refilling or replenishing the inner tank (3) and the outer container (5) with cold water and mixing the water in the inner tank (3) and in the outer container (5) such that the temperature differential required for a further measurement is formed.

4. Process according to claim 1, wherein as much water heated by a combustion process is transferred from the inner tank (3) into the outer container (5) that the water situated in the outer container (5) has a temperature too high for the next measurement, and further comprising the exact temperature differential in relation to the inner tank (3) by replenishing of cold or water not tempered.

5. Process according to claim 1, wherein the temperature in the inner tank (3) and in the outer container (5) is measured while transferring heated water into the outer container (5) and while replenishing with cold water, and the supply of the water to be replenished is regulated through valves or other means (9, 22, 28).

6. Process according to claim 1, wherein the water temperature is recorded during filling and temperature adjustment in the inner tank (3) and the resulting mixture temperature of the water is estimated in advance by a computer and the tempering of the water in the outer container (5) takes place prior to the end of the temperature balancing in the inner tank (3) between the water introduced, the calorimetric bomb (2) and the inner partition.

7. Device for conducting the process according to claim 1, comprising a calorimeter with an inner tank (3) accommodating a calorimetric bomb (2) and with an outer container (5) enclosing the inner tank with a distance (4) for accommodating a water jacket (6) as well as with a water feed (7) to the inner tank (3) and the outer container (5), and with a water drain at least on the outer container, and furthermore with a heating device arranged in the water feed (7) which is preferably connected with a regulating device (15), whereby temperature sensors are arranged in the outer container (5) and in the inner tank (3) which are connected with the regulating device for the water feed, the water feed (7) to the outer container (5) and to the inner container (3) is arranged in the lower region, and a drain or overflow (21) is arranged in an upper edge region (20) of the outer container (5), and the feed to the inner tank (3) is switchable and usable as a discharge.

8. Device according to claim 7, wherein a single water feed (7) is provided with a branching (23), and from the branching, a feeder (24) at all times leads to the outer container (5) and a further feeder (25) leads to the inner tank, and a portion of the feeder (25) to the inner tank (3) is usable as a drain and is lockably connected through a valve (22) with the branching (23) and the feeder (24) to the outer container (5).

9. Device according to claim 7, wherein a continuous flow heater (10) is arranged in the feed conduit (12) before the branching (23) for tempering the water.

10. Device according to claim 7, wherein the water feed is connected or connectable with a stationarily installed water conduit.

11. Device according to claim 7, wherein at least the wall of the outer container (5) includes partitions that are heat-insulated.

12. Device according to claim 7, wherein an agitator (26) is arranged in the inner tank (3), for mixing the water in the inner tank (3), and a pump (27) is arranged in an outlet conduit (21) of the outer container (5).

13. Device according to claim 7, wherein a valve (28) which is closed during measurement is arranged behind the pump (27) in the discharge direction of the water which can be sucked or discharged out of the outer container (27).

14. Device according to claim 7, wherein on the upper side of the inner tank (3), a cover is arranged, which bounds on its underside facing the interior of the inner tank (3) a space in particular conically tapering upward on the highest point of which a filling level sensor (31) is arranged, and the cover (29) is sealed off against the inner tank (3) through a capillary slot (32).

15. Device according to claim 14, wherein an additional annular slot (33) is arranged above the capillary slot (32), for accommodating water exiting due to expansion during heating.

* * * * *